(12) United States Patent
Thormann et al.

(10) Patent No.: US 7,504,436 B2
(45) Date of Patent: Mar. 17, 2009

(54) BIOISOSTERES OF ACTINONIN

(75) Inventors: Michael Thormann, Martinsried (DE); Michael Almstetter, Grasbrunn (DE)

(73) Assignee: Novartis AG, Basel (CH)

( * ) Notice: Subject to any disclaimer, the term of this patent is extended or adjusted under 35 U.S.C. 154(b) by 120 days.

(21) Appl. No.: 10/556,175

(22) PCT Filed: May 7, 2004

(86) PCT No.: PCT/EP2004/004902

§ 371 (c)(1),
(2), (4) Date: Jun. 5, 2006

(87) PCT Pub. No.: WO2004/099124

PCT Pub. Date: Nov. 18, 2004

(65) Prior Publication Data

US 2007/0060624 A1    Mar. 15, 2007

(30) Foreign Application Priority Data

May 8, 2003    (DE) ................. 103 20 453

(51) Int. Cl.
*A61K 31/185*    (2006.01)
*C07C 259/06*    (2006.01)
(52) U.S. Cl. .................... 514/575; 562/623
(58) Field of Classification Search ............ None
See application file for complete search history.

(56) References Cited

U.S. PATENT DOCUMENTS

| | | | | |
|---|---|---|---|---|
| 4,122,186 A * | 10/1978 | Lafon | ............ | 514/575 |
| 5,994,351 A * | 11/1999 | Robinson et al. | ......... | 514/237.5 |
| 2002/0198241 A1* | 12/2002 | Hunter et al. | ............ | 514/357 |
| 2003/0166687 A1* | 9/2003 | Warpehoski et al. | ........ | 514/341 |

FOREIGN PATENT DOCUMENTS

| | | | | |
|---|---|---|---|---|
| WO | WO 96/26918 A | * | 9/1996 | |
| WO | WO 02/28829 A | * | 4/2002 | |

OTHER PUBLICATIONS

Ramadan et al. Journal Of Chromatography. 1985, vol. 321, No. 1, pp. 81-91.*
Ahuja et al. Carbohydrate Polymers, Applied Science. May. 1997, vol. 33, No. 1, pp. 57-62.*
Mumford et al. Biochemical And Biophysical Research Communications. 1982, vol. 109, No. 4, pp. 1303-1309.*
Greiner et al. Letters In Peptide Science. 2000, vol. 7, No. 3, pp. 133-144.*
Ewenson et al. European Journal Of Medicinal Chemistry. 1992, vol. 27, No. 3, pp. 179-186.*
Thorarensen et al. Bioorganic & Medicinal Chemistry Letters. 2001, vol. 11, pp. 1355-1358.*
Nishino et al. Design of Potent Reversible Inhibitors of Thermolysin. Biochemistry. 1979, vol. 18, No. 20, pp. 4340-4347.*
S.Bohra et al. Synthesis of New Polymer Supported Chelating Resins. J. Polym. Mater; 9; (1992), pp. 319-320.

* cited by examiner

*Primary Examiner*—Jeffrey E Russel
(74) *Attorney, Agent, or Firm*—Edwards Angell Palmer & Dodge LLP; Peter F. Corless; Nicholas J. DiCeglie, Jr.

(57) ABSTRACT

The present invention relates to novel bioisosteres of the antibiotic actinonin of the general formula (I). The novel compounds are of particular interest as inhibitors of metalloproteinases.

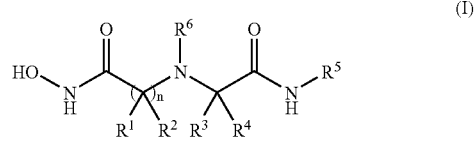

(I)

9 Claims, No Drawings

BIOISOSTERES OF ACTINONIN

The present invention relates to novel bioisosteres of the antibiotic actinonin. The novel compounds are of particular interest as inhibitors of metalloproteinases.

Actinonin (A) is an antibiotic having antibacterial activity that is obtained by fermentation of an actinomycetes strain (U.S. Pat. No. 3,240,787).

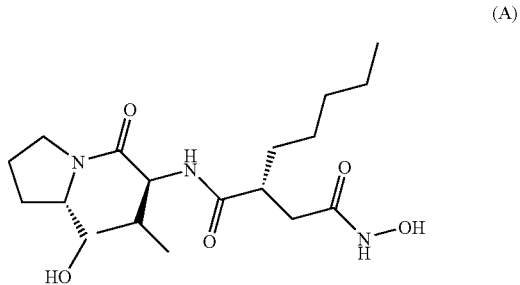

(A)

Actinonin inhibits numerous enzymes, such as, for example, peptidases, metalloproteinases, encephalinase and ACE. It has recently been described that actinonin inhibits peptide deformylase (PDF) (C. Giglione, T. Meinnel, Emerging Therapeutic Targets 2001, 5(1), 41-57).

The aim of the present invention was to provide novel analogues of actinonin that are synthetically accessible by a simple route. The compounds are of great interest especially as inhibitors of metalloproteinases (especially of PDF).

The present invention relates to compounds of the formula (I)

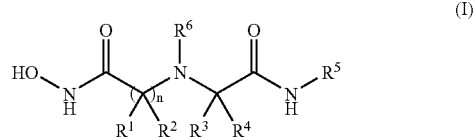

(I)

wherein $R^1$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^2$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^3$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^4$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^5$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

$R^6$ is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

or two of the radicals $R^1$, $R^2$, $R^3$, $R^4$ and $R^6$ together are part of an optionally substituted cycloalkyl or heterocycloalkyl ring and n is 1, 2 or 3, or a pharmaceutically acceptable salt, solvate or hydrate or a pharmaceutically acceptable formulation thereof.

The term alkyl refers to a saturated, straight-chain or branched hydrocarbon group having from 1 to 20 carbon atoms, preferably from 1 to 12 carbon atoms, especially from 1 to 6 carbon atoms, for example the methyl, ethyl, propyl, isopropyl, isobutyl, tert-butyl, n-hexyl, 2,2-dimethylbutyl or n-octyl group.

The terms alkenyl and alkynyl refer to at least partially unsaturated, straight-chain or branched hydrocarbon groups having from 2 to 20 carbon atoms, preferably from 2 to 12 carbon atoms, especially from 2 to 6 carbon atoms, for example the ethenyl, allyl, acetylenyl, propargyl, iso-prenyl and hex-2-enyl groups. Preferably, alkenyl groups have one or two (especially one) double bond(s) and alkynyl groups have one or two (especially one) triple bond(s).

Furthermore, the terms alkyl, alkenyl and alkynyl refer to groups in which one or more hydrogen atoms have been replaced by a halogen atom (preferably F or Cl), such as, for example, the 2,2,2-trichloroethyl group and the trifluoromethyl group.

The term heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulphur atom (preferably oxygen, sulphur or nitrogen). The term heteroalkyl refers also to a carboxylic acid or a group derived from a carboxylic acid, such as, for example, acyl, acyl-alkyl, alkoxycarbonyl, acyloxy, acyloxyalkyl, carboxy-alkylamide or alkoxycarbonyloxy.

Examples of heteroalkyl groups are groups of the formulae $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ is a hydrogen atom or a $C_1$-$C_6$alkyl, $C_2$-$C_6$alkenyl or $C_2$-$C_6$alkynyl group; $R^b$ is a hydrogen atom or a $C_1$-$C_6$alkyl, $C_2$-$C_6$alkenyl or $C_2$-$C_6$alkynyl group; $R^c$ is a hydrogen atom or a $C_1$-$C_6$alkyl, $C_2$-$C_6$alkenyl or $C_2$-$C_6$alkynyl group; $R^d$ is a hydrogen atom or a $C_1$-$C_6$alkyl, $C_2$-$C_6$alkenyl or $C_2$-$C_6$alkynyl group; and $Y^a$ is a direct bond or a $C_1$-$C_6$alkylene, $C_2$-$C_6$alkenylene or $C_2$-$C_6$alkynylene group, wherein each heteroalkyl group contains at least one carbon atom and one or more hydrogen atoms may have been replaced by fluorine or chlorine atoms. Specific examples of heteroalkyl groups are methoxy, trifluoromethoxy, ethoxy, n-propyloxy, isopropyloxy, tert-butoxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups.

The term cycloalkyl refers to a saturated or partially unsaturated (for example cycloalkenyl) cyclic group having one or more rings (preferably 1 or 2) that form a structure containing from 3 to 14 carbons atoms, preferably from 3 to 10 (especially 3, 4, 5, 6 or 7) carbon atoms. The term cycloalkyl refers also to groups in which one or more hydrogen atoms have been replaced by fluorine, chlorine, bromine or iodine atoms or OH, $=$O, SH, $=$S, NH$_2$, $=$NH or NO$_2$ groups, that is to say, for example, cyclic ketones, such as, for example, cyclohexanone, 2-cyclohexenone or cyclopentanone. Further specific examples of cycloalkyl groups are cyclopropyl, cyclobutyl, cyclopentyl, spiro-[4,5]decanyl, norbornyl, cyclohexyl, cyclopentenyl, cyclohexadienyl, decalinyl, cubanyl, bicyclo[4.3.0]nonyl, Tetralin, cyclopentylcyclohexyl, fluorocyclohexyl and cyclohex-2-enyl groups.

The term heterocycloalkyl refers to a cycloalkyl group as defined above wherein one or more (preferably 1, 2 or 3) ring carbon atoms have been replaced by an oxygen, nitrogen, silicon, selenium, phosphorus or sulphur atom (preferably oxygen, sulphur or nitrogen). A heterocycloalkyl group preferably has 1 or 2 rings with from 3 to 10 (especially 3, 4, 5, 6 or 7) ring atoms. The term heterocycloalkyl refers also to groups in which one or more hydrogen atoms have been replaced by fluorine, chlorine, bromine or iodine atoms or OH, $=$O, SH, $=$S, NH$_2$, $=$NH or NO$_2$ groups. Examples are the piperidyl, morpholinyl, urotropinyl, pyrrolidinyl, tetrahydrothiophenyl, tetrahydropyranyl, tetrahydrofuryl, oxacyclopropyl, aza-cyclopropyl and 2-pyrazolinyl groups, as well as lactams, lactones, cyclic imides and cyclic anhydrides.

The term alkylcycloalkyl refers to groups that in accordance with the above definitions contain both cycloalkyl and alkyl, alkenyl or alkynyl groups, for example alkylcycloalkyl, alkylcycloalkenyl, alkenylcycloalkyl and alkynylcycloalkyl groups. An alkylcycloalkyl group preferably contains a cycloalkyl group having one or two ring systems that form a structure containing from 3 to 10 (especially 3, 4, 5, 6 or 7) carbon atoms and one or two alkyl, alkenyl or alkynyl groups having from 1 or 2 to 6 carbon atoms.

The term heteroalkylcycloalkyl refers to alkylcycloalkyl groups, as defined above, in which one or more (preferably 1, 2 or 3) carbon atoms have been replaced by an oxygen, nitrogen, silicon, selenium, phosphorus or sulphur atom (preferably oxygen, sulphur or nitrogen). A heteroalkylcycloalkyl group preferably has 1 or 2 ring systems with from 3 to 10 (especially 3, 4, 5, 6 or 7) ring atoms and one or two alkyl, alkenyl, alkynyl or heteroalkyl groups having from 1 or 2 to 6 carbon atoms. Examples of such groups are alkylheterocycloalkyl, alkyl-heterocycloalkenyl, alkenyl-heterocycloalkyl, alkynyl-heterocycloalkyl, heteroalkylcycloalkyl, heteroalkyl-heterocycloalkyl and heteroalkyl-heterocycloalkenyl, the cyclic groups being saturated or mono-, di- or tri-unsaturated.

The term aryl or Ar refers to an aromatic group that has one or more rings and is formed by a structure containing from 6 to 14 carbon atoms, preferably from 6 to 10 (especially 6) carbon atoms. The term aryl (or Ar) refers also to groups in which one or more hydrogen atoms have been replaced by fluorine, chlorine, bromine or iodine atoms or OH, SH, NH$_2$ or NO$_2$ groups. Examples are phenyl, naphthyl, biphenyl, 2-fluorophenyl, anilinyl, 3-nitrophenyl and 4-hydroxyphenyl groups.

The term heteroaryl refers to an aromatic group that has one or more rings and is formed by a structure containing from 5 to 14 ring atoms, preferably from 5 to 10 (especially 5 or 6) ring atoms and one or more (preferably 1, 2, 3 or 4) oxygen, nitrogen, phosphorus or sulphur ring atoms (preferably O, S or N). The term heteroaryl refers also to groups in which one or more hydrogen atoms have been replaced by fluorine, chlorine, bromine or iodine atoms or OH, SH, NH$_2$ or NO$_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl groups.

The term aralkyl refers to groups that in accordance with the above definitions contain both aryl and alkyl, alkenyl, alkynyl and/or cycloalkyl groups, such as, for example, arylalkyl, arylalkenyl, arylalkynyl, arylcycloalkyl, arylcycloalkenyl, alkylarylcycloalkyl and alkyl-arylcycloalkenyl groups. Specific examples of aralkyls are toluene, xylene, mesitylene, styrene, benzyl chloride, o-fluorotoluene, 1H-indene, Tetralin, dihydronaphthalenes, indanone, phenylcyclopentyl, cumene, cyclohexylphenyl, fluorene and indane. An aralkyl group preferably contains one or two aromatic ring systems (1 or 2 rings) with from 6 to 10 carbon atoms and one or two alkyl, alkenyl and/or alkynyl groups having from 1 or 2 to 6 carbon atoms and/or a cycloalkyl group having 5 or 6 ring carbon atoms.

The term heteroaralkyl refers to an aralkyl group as defined above, in which one or more (preferably 1, 2, 3 or 4) carbon atoms have been replaced by an oxygen, nitrogen, silicon, selenium, phosphorus, boron or sulphur atom (preferably oxygen, sulphur or nitrogen), that is to say groups that in accordance with the above definitions contain both aryl or heteroaryl and alkyl, alkenyl, alkynyl and/or heteroalkyl and/or cycloalkyl and/or heterocycloalkyl groups. A heteroaralkyl group preferably contains one or two aromatic ring systems (1 or 2 rings) with from 5 or 6 to 10 carbon atoms and one or two alkyl, alkenyl and/or alkynyl groups having from 1 or 2 to 6 carbon atoms and/or a cycloalkyl group having 5 or 6 ring carbon atoms, with 1, 2, 3 or 4 of those carbon atoms having been replaced by oxygen, sulphur or nitrogen atoms.

Examples are aryl-heteroalkyl, aryl-heterocycloalkyl, aryl-heterocycloalkenyl, arylalkyl-heterocycloalkyl, arylalkenyl-heterocycloalkyl, arylalkynyl-heterocycloalkyl, arylalkyl-heterocycloalkenyl, heteroarylalkyl, heteroarylalkenyl, heteroarylalkynyl, heteroaryl-heteroalkyl, heteroarylcycloalkyl, heteroarylcycloalkenyl, heteroaryl-heterocycloalkyl, heteroaryl-heterocycloalkenyl, heteroarylalkylcycloalkyl, heteroarylalkyl-heterocycloalkenyl, heteroaryl-heteroalkylcycloalkyl, heteroaryl-heteroalkylcycloalkenyl and heteroaryl-heteroalkyl-heterocycloalkyl groups, the cyclic groups being saturated or mono-, di- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl and 2-, 3- or 4-carboxylphenylalkyl groups.

The terms cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced by fluorine, chlorine, bromine or iodine atoms or OH, $=$O, SH, $=$S, NH$_2$, $=$NH or NO$_2$ groups.

The expression "optionally substituted" refers to groups in which one or more hydrogen atoms have been replaced by fluorine, chlorine, bromine or iodine atoms or OH, =O, SH, =S, $NH_2$, =NH or $NO_2$ groups. The expression refers also to groups substituted by unsubstituted $C_1$-$C_6$alkyl, $C_2$-$C_6$-alkenyl, $C_2$-$C_6$alkynyl, $C_1$-$C_6$heteroalkyl, $C_3$-$C_{10}$cycloalkyl, $C_2$-$C_9$heterocycloalkyl, $C_6$-$C_{10}$aryl, $C_1$-$C_9$heteroaryl, $C_7$-$C_{12}$-aralkyl or $C_2$-$C_{11}$heteroaralkyl groups.

Compounds of the formula (I) may by virtue of their substitution contain one or more centres of chirality. The present invention therefore includes all pure enantiomers and all pure diastereoisomers as well as mixtures thereof in any mixing ratio. The present invention also includes all cis/trans isomers of the compounds of the general formula (I) as well as mixtures thereof. The present invention also includes all tautomeric forms of the compounds of the formula (I).

Preference is given to compounds of the formula (I) wherein $R^1$ is a hydrogen atom.

Preference is also given to compounds of the formula (I) wherein $R^2$ is a hydrogen atom.

Preference is in turn given to compounds of the formula (I) wherein n is 1.

Also preferred are compounds of the formula (I) wherein $R^3$ is a hydrogen atom.

Preference is in turn given to compounds of the formula (I) wherein $R^6$ is a hydrogen atom.

Examples of pharmacologically acceptable salts of compounds of the formula (I) are salts of physiologically acceptable mineral acids, such as hydrochloric acid, sulphuric acid and phosphoric acid; or salts of organic acids, such as methanesulphonic acid, p-toluenesulphonic acid, lactic acid, formic acid, acetic acid, trifluoroacetic acid, citric acid, succinic acid, fumaric acid, maleic acid and salicylic acid. Compounds of the formula (I) may be in solvated form, especially in hydrated form. Hydrate formation can occur, for example, during the preparation process or as a consequence of the hygroscopic nature of the initially anhydrous compounds of the formula (I).

The pharmaceutical compositions according to the present invention comprise at least one compound of the formula (I) as active ingredient and optionally carriers and/or adjuvants.

The pro-drugs (for example R. B. Silverman, Medizinische Chemie, V C H Weinheim, 1995, Chapter 8, page 361 ff), to which the present invention also relates, consist of a compound of the formula (I) or (II) and at least one pharmacologically acceptable protecting group that is removed under physiological conditions, for example a hydroxy, alkoxy, aralkyloxy, acyl or acyloxy group, such as, for example, a methoxy, ethoxy, benzyloxy, acetyl or acetyloxy group.

The present invention relates also to the therapeutic use of the compounds of the formula (I), their pharmacologically acceptable salts and solvates and hydrates as well as formulations and pharmaceutical compositions.

The present invention relates also to the use of those active ingredients in the production of medicaments for preventing and/or treating diseases, especially those diseases mediated by PDF. Compounds of the formula (I) are generally administered using the known and acceptable methods, either on their own or in combination with any desired other therapeutic agent. Administration can be effected, for example, by one of the following methods: orally, for example in the form of dragées, coated tablets, pills, semi-solid preparations, soft or hard capsules, solutions, emulsions or suspensions; parenterally, for example in the form of an injectable solution; rectally in the form of suppositories; by inhalation, for example in the form of a powder formulation or spray; transdermally or intranasally. For the production of such tablets, pills, semi-solid preparations, coated tablets, dragées and hard gelatin capsules, the therapeutically acceptable product can be mixed with pharmacologically inert, inorganic or organic pharmaceutical carrier substances, for example with lactose, sucrose, glucose, gelatin, malt, silica gel, starch or derivatives thereof, talcum, stearic acid or salts thereof, skimmed milk powder and the like. For the production of soft capsules, pharmaceutical carriers such as, for example, vegetable oils, petroleum, animal or synthetic oils, wax, fat and polyols can be used. For the production of liquid solutions and syrups, pharmaceutical carriers such as, for example, water, alcohols, aqueous saline solution, aqueous dextrose, polyols, glycerol, vegetable oils, petroleum and animal or synthetic oils can be used. For suppositories, pharmaceutical carriers such as, for example, vegetable oils, petroleum, animal or synthetic oils, wax, fat and polyols can be used. For aerosol formulations, compressed gases suitable for that purpose can be used, such as, for example, oxygen, nitrogen and carbon dioxide. The pharmaceutically acceptable preparations can also comprise additives for preserving, stabilising, emulsifiers, sweeteners, flavourings, salts for altering the osmotic pressure, buffers, coating additives and anti-oxidants.

Compounds of the formula (I) can be prepared by means of an Ugi 3-component reaction (for example A. Dömling, I. Ugi, Angew. Chem. 2000, 112, 3300-3344) with subsequent conversion of the ester used into the hydroxamic acid:

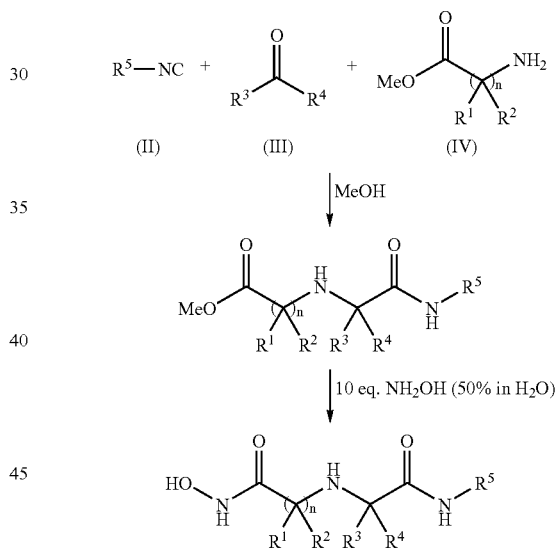

EXAMPLES

General Procedure:

1 mmol of isonitrile (II), 1 mmol of carbonyl compound (III) and 1 mmol of amino acid derivative (IV) are dissolved in 5 ml of methanol and stirred at room temperature for 24 hours. If desired, the reaction may be carried out in the presence of a catalyst, such as, for example, p-toluenesulphonic acid or $BF_3$*$Et_2O$. Then 10 equivalents of hydroxylamine (50% in $H_2O$) are added and stirring is carried out for a further 12 hours. After removal of the solvent, any protecting groups present are removed and the desired product is then purified by means of HPLC.

The following compounds were prepared in accordance with the general procedure and characterised by means of HPLC-MS and LCMS-CLND.

7
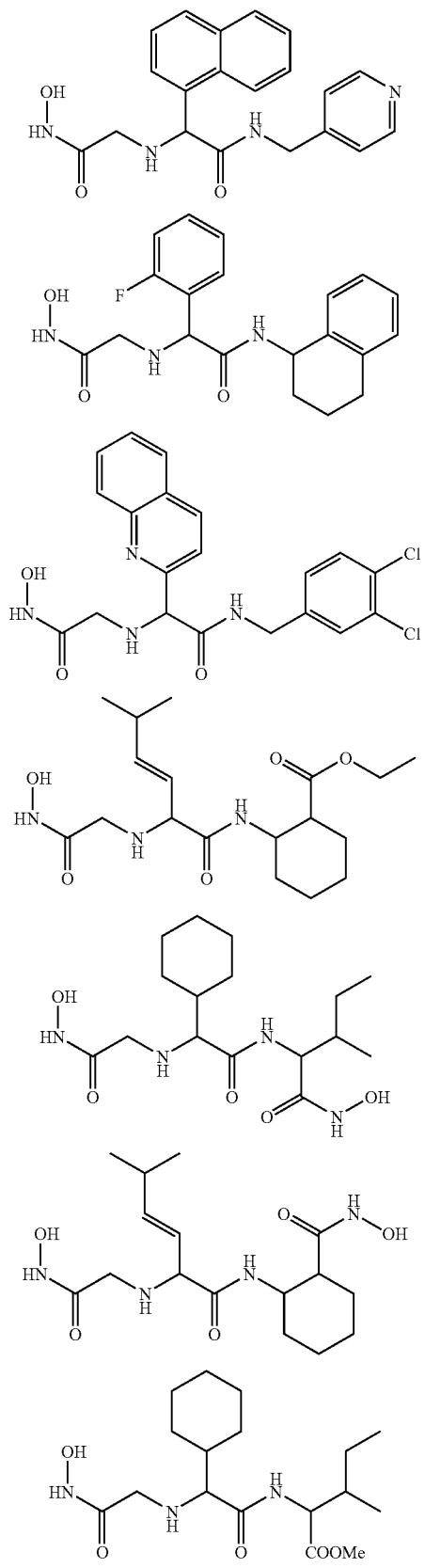
8
-continued
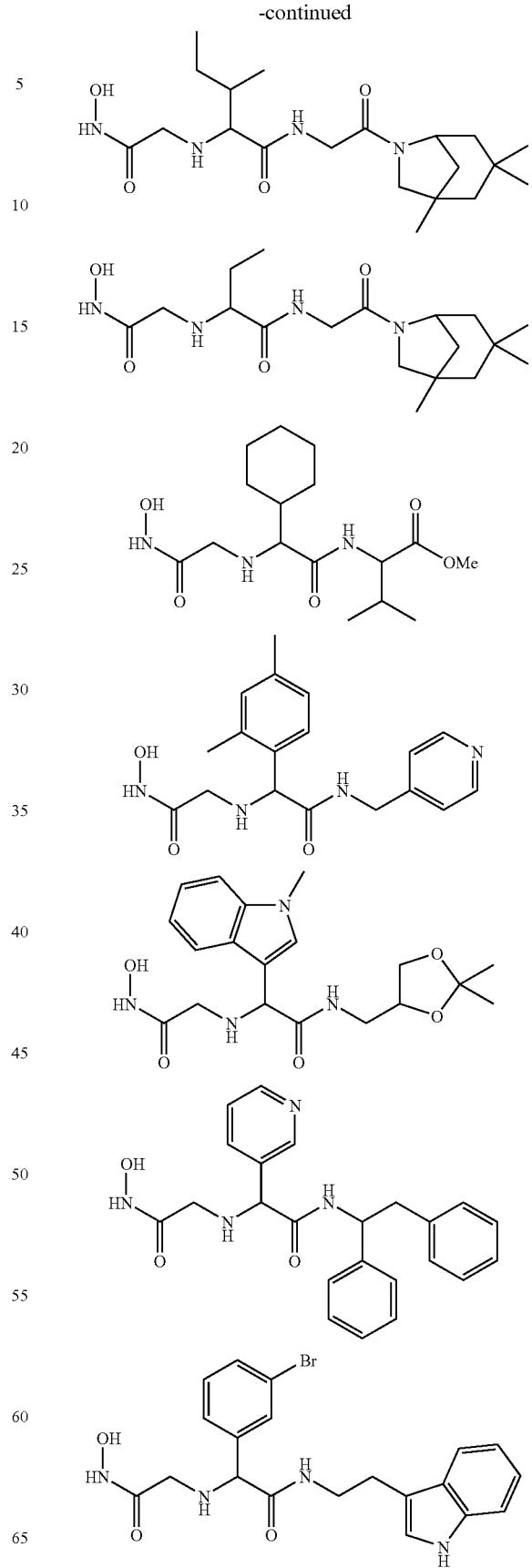

-continued
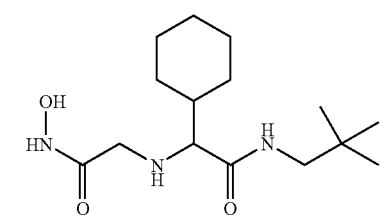
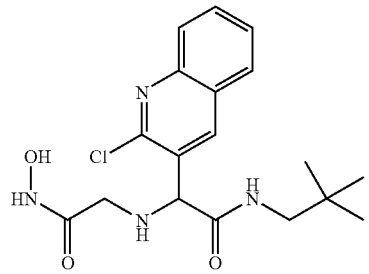
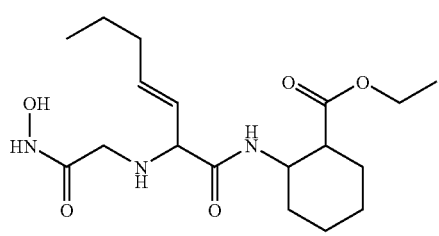
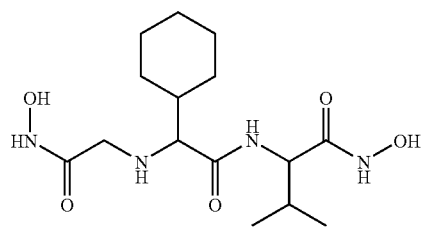
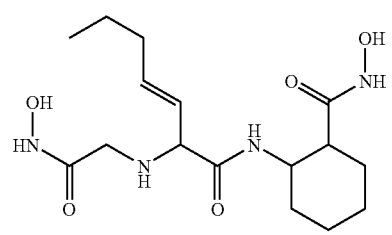
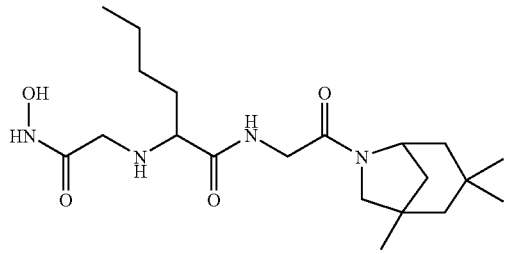
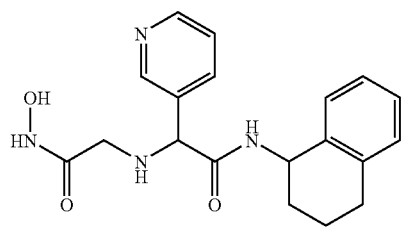
-continued
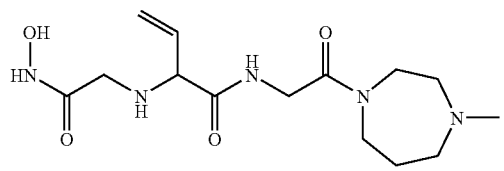
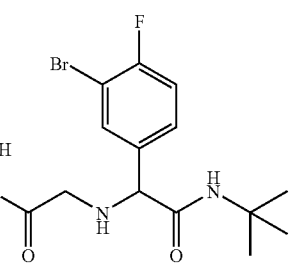
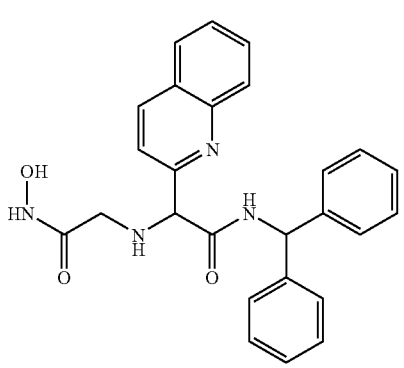
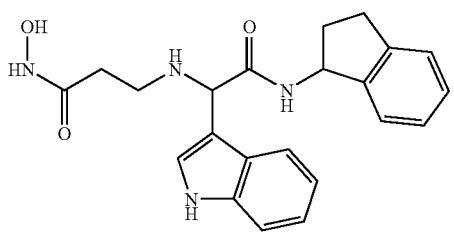
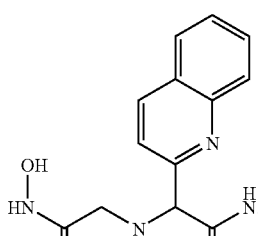
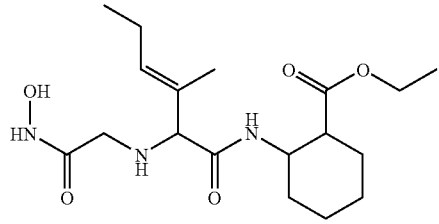

-continued
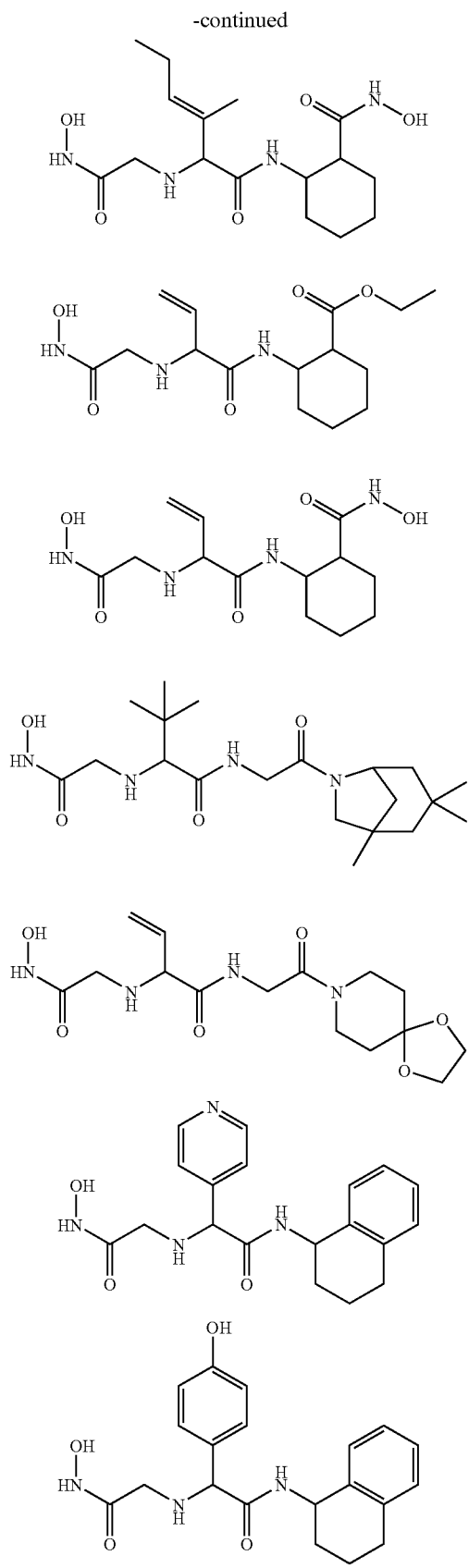
-continued
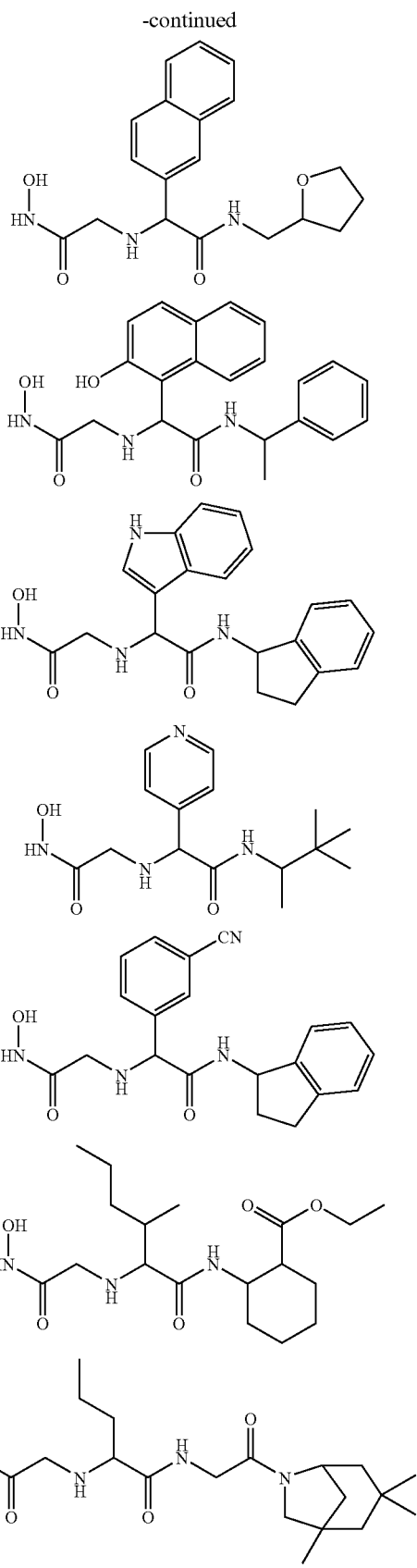

-continued

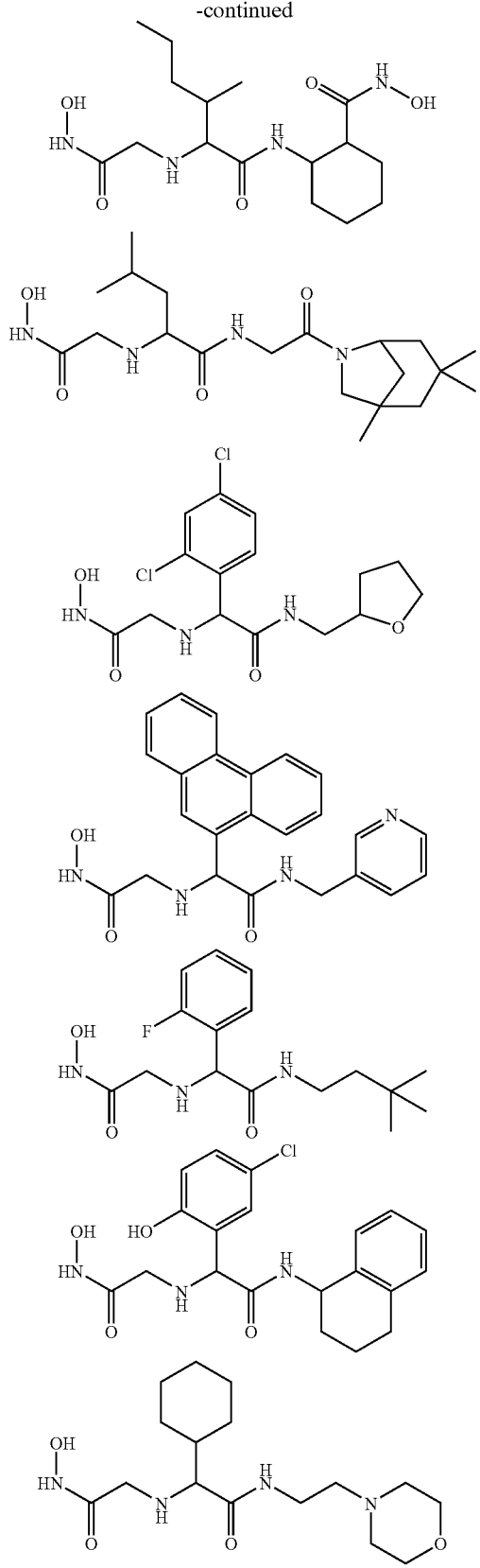

The invention claimed is:

1. A compound of the formula (I)

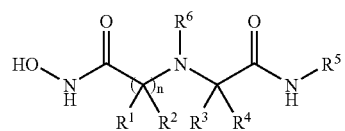

wherein

R[1] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R[2] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R[3] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R[4] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R[5] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R[6] is a hydrogen atom or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

or two of the radicals R[1], R[2], R[3], R[4] and R[6] together are part of an optionally substituted cycloalkyl or heterocycloalkyl ring and n is 1, or a pharmaceutically acceptable salt, solvate or hydrate or a pharmaceutically acceptable formulation thereof.

2. A compound of claim 1 wherein R[1] is a hydrogen atom.

3. A compound of claim 2 wherein R[2] is a hydrogen atom.

4. A compound of claim 1 wherein R[3] is a hydrogen atom.

5. A compound of claim 1 wherein R[6] is a hydrogen atom.

6. A pharmaceutical composition comprising a compound of claim 1.

7. The pharmaceutical composition of claim 6 further comprising one or more carriers and/or one or more adjuvants.

8. A method for treating a subject in need of inhibition of metalloproteinases, comprising administering to the subject one or more compounds of claim 1.

9. A method for treating a subject suffering from or susceptible to a disease mediated by metalloproteinase activity, comprising administering to the subject one or more compounds of claim 1.

* * * * *